United States Patent [19]

Weissman

[11] 4,449,937

[45] May 22, 1984

[54] DENTAL ANCHOR

[75] Inventor: Bernard Weissman, New York, N.Y.

[73] Assignee: Ipco Corporation, White Plains, N.Y.

[21] Appl. No.: 326,851

[22] Filed: Dec. 3, 1981

[51] Int. Cl.[3] .............................................. A61C 5/08
[52] U.S. Cl. .................................................... 433/225
[58] Field of Search ......................................... 433/225

[56] References Cited

U.S. PATENT DOCUMENTS

| 1,743,910 | 1/1930 | Bortner | 433/225 |
| 3,395,455 | 8/1968 | Overby et al. | 433/225 |
| 4,331,423 | 5/1982 | Yanney | 433/225 |
| 4,365,958 | 12/1982 | Vlock | 433/25 |

Primary Examiner—Robert Peshock
Attorney, Agent, or Firm—Goodman & Teitelbaum

[57] ABSTRACT

A dental anchor for securing a superstructure to a tooth understructure, the dental anchor having a forward elongated anchoring portion for insertion into a channel extending into the tooth understructure. A coaxial, elongated retaining portion extends from the anchoring portion and has a non-circular cross sectional configuration to provide displacement resistant properties for retaining the superstructure. A depth-limiting portion is integrally disposed between the anchoring portion and the retaining portion for limiting the depth of insertion of the anchoring portion into the channel. The depth-limiting portion has a frustro-conical section which sits into a countersink formed at the upper end of the channel in the tooth understructure. A dental tool is provided to form a limited depth channel simultaneously with a countersink in the tooth understructure for use in conjunction with the dental anchor.

13 Claims, 13 Drawing Figures

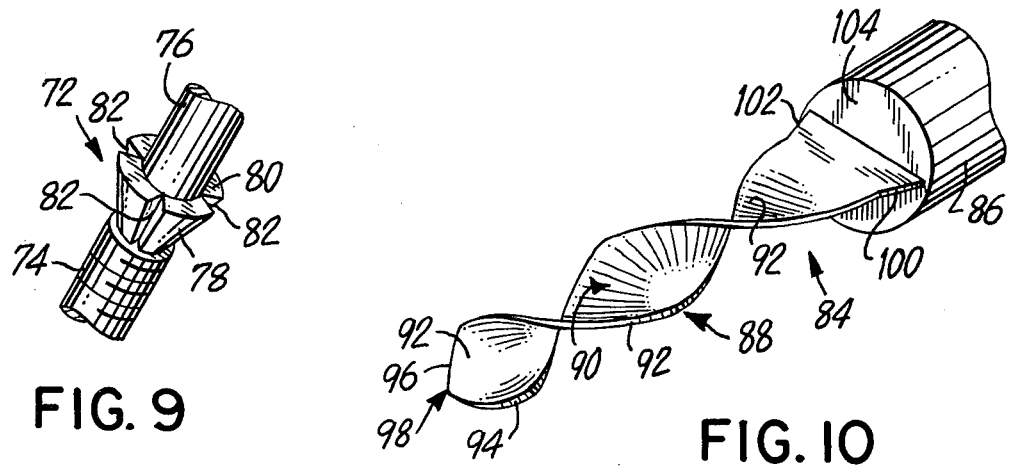
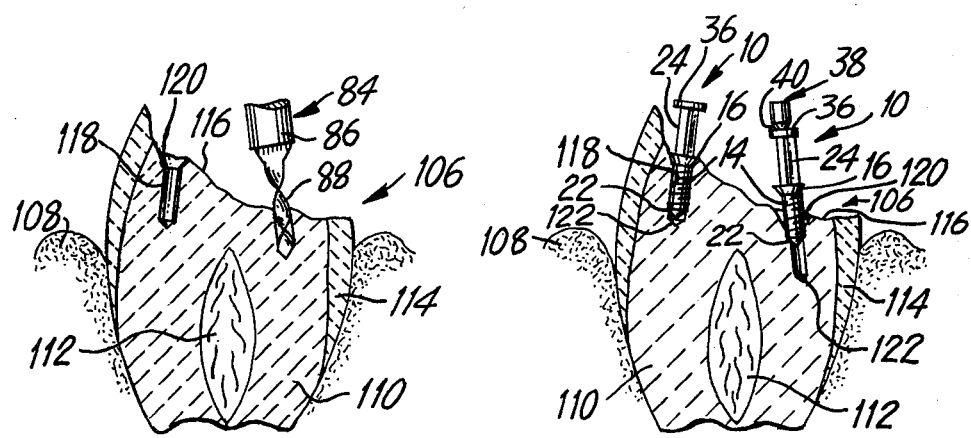
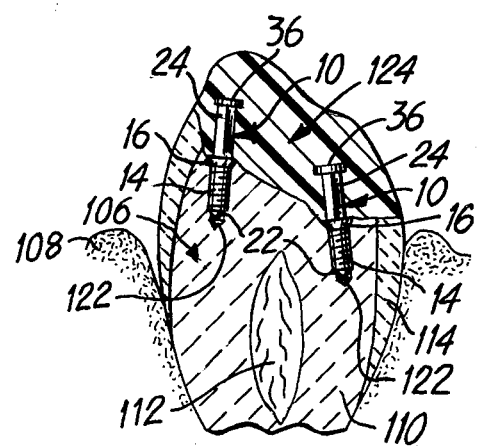

DENTAL ANCHOR

BACKGROUND OF THE INVENTION

This invention relates to dentistry, and more particularly to apparatus utilized for building a superstructure on broken or undermined dentition.

Where a portion of tooth is broken, decayed or the like, one dental technique is to remove the decayed or broken portion of the dentition so as to define a tooth understructure. A number of channels are then drilled in the understructure and rods are threaded into these channels with a portion of the rods projecting above the surface of the understructure. A superstructure is then built on this surface so as to adhere onto the portion of the rods extending above the understructure. This method is described in detail in my U.S. Pat. No. 3,434,209.

The particular metal rods or dental anchors which are utilized to interconnect the superstructure and anchor it onto the understructure, have been of various types. For example, in my U.S. Pat. No. 3,675,328, there is described a dental anchor having a plurality of threaded sections with each section being capable of being severed apart from the other. In my U.S. Pat. No. 3,675,329, there is provided an anchoring pin with a head, wherein the head extends above the understructure so as to be received in the superstructure and provide a displacement-resisting portion in the superstructure. A further dental anchor is provided in my U.S. Pat. No. 4,053,982, which utilizes an L-shaped manipulating portion which can be received in a dental tool for manipulating the anchor into the understructure. Various types of manipulating portions can also be provided on the dental anchor, as shown in my U.S. Pat. No. 4,202,101, which also describes a hand held driver for use in inserting the dental anchor in the understructure.

Although each of these prior art metal dental anchors and related apparatus have been exceedingly useful, specific problems have been noted when using this dental technique. One problem concerns the cracking of the understructure as the dental anchor is being threaded into it. Typically, the channel is provided in the understructure and the anchor is then threaded into that channel. In most cases, a self-threading arrangement is provided on the dental anchor, so that the insertion of the anchor in the channel self-threads into the understructure. During this threading, and typically upon reaching the bottom of the channel, cracks can form in the understructure.

Another problem is the suitable retention of the superstructure firmly in position on the understructure. The technique must include a provision for preventing rotation or displacement of the superstructure with respect to the understructure. In the various prior art arrangements, it has been provided to retain part of the threaded portion of the anchor projecting above the understructure to retain the superstructure. Additionally, an enlarged head has been provided on the threaded portion of the anchor for embedding in the superstructure.

Also, by inclining the anchors in the understructure, the angled arrangement provides additional adhesion within the superstructure. It is also possible to bend over a portion of the threaded anchor above the understructure so as to provide additional retention within the superstructure and thus provide a further displacement resistant accommodation.

Nevertheless, further improvement would be desired in retaining the superstructure in place and avoiding displacement of the superstructure after it has been secured onto the understructure.

SUMMARY OF THE INVENTION

Accordingly, it is an object of the present invention to provide an improved means for building a superstructure on a broken or undetermined dentition.

Another object of the present invention is to provide an ixproved dental anchor for use in anchoring a superstructure to an understructure of the tooth so as to avoid displacement of the superstructure after it has been secured in place.

Another object of the present invention is to provide a dental anchor for use in retaining a superstructure onto an understructure, wherein the dental anchor is fabricated from a plastic material.

A further object of the present invention is to provide a dental anchor for use in retaining a superstructure onto an understructure, and which avoids the possibility of cracks forming in the understructure.

Yet another object of the present invention is to provide an improved dental anchor which includes a depth-limiting portion so as to avoid bottoming out of the anchor in the channel formed in the understructure, thereby avoiding the possibility of cracks forming in the understructure.

An added object of the present invention is to provide an improved dental anchor which includes an annular portion which can fit into a countersink formed at the mouth of a channel formed in the understructure.

Still a further object of the present invention is to provide a dental anchor having an anchoring portion which can provide self-threading into a tooth understructure, and which also automatically forms a countersink in the tooth understructure to limit the depth of insertion of the anchor in the tooth understructure.

A further object of the present invention is to provide a dental anchor having a lower anchoring portion for insertion into the tooth understructure and an upper retaining portion having a non-circular shape so as to provide unique retention in the tooth superstructure and avoid displacement of such superstructure with respect to the understructure.

Another object of the present invention is to provide a tool for forming a channel of limited depth in a tooth understructure.

Still another object of the present invention is to provide a dental tool for simultaneously forming a channel with a countersink in a tooth understructure.

Yet another object of the present invention is to provide a simple dental tool for use in the formation of channels in tooth understructure for subsequent limited insertion of dental anchors in such channels.

These objects are achieved in accordance with the present invention, wherein there is provided a dental anchor for securing a superstructure to a tooth understructure.

The dental anchor includes an elongated anchoring portion which can be inserted within a channel formed in a tooth understructure. A coaxial, elongated retaining portion extends from the anchoring portion, the retaining portion being embedded within the tooth superstructure. The retaining portion has a non-circular cross sectional configuration. Integrally disposed between the anchoring portion and the retaining portion, is a depth-limiting portion which limits the depth of insertion of the anchoring portion into the channel of the understructure.

The anchoring portion is typically threaded and the depth-limiting portion can typically be flat-head at the upper end of the threaded portion. More particularly, it is formed of a frustro-conical section which flares outwardly from the anchoring portion and can seat in a countersink formed at the upper end of the channel. In an exbodiment of the invention, the frustro-conical section includes a plurality of elongated notches about its periphery so that rotational insertion of the anchoring portion in the channel self-forms a countersink in the tooth understructure.

The dental anchor can be a molded pin fabricated from a suitable plastic material, or a machined pin fabricated from a suitable metal material.

Additionally, a dental tool is provided having a conventional shank with a blade extending from the shank portion. The blade is a thin piece of metal twisted 360 degrees so as to form a twist drill. The lateral edges of the blade portion joining the blade to the shank portion are outwardly flared, whereby a countersink can be automatically formed at the upper end of a channel which is drilled. Typically, the blade portion is embedded in the shank portion and the forward end of the shank portion serves as a stop for limiting the depth of the channel being formed.

BRIEF DESCRIPTION OF THE DRAWINGS

With the above and additional objects and advantages in view, as will hereinafter appear, this invention comprises the devices, combinations and arrangements of parts hereinafter described by way of example, and illustrated in the accompanying drawings of preferred embodiments in which:

FIG. 9 is a perspective view showing an embodiment of the depth-limiting portion of the dental anchor;

FIG. 10 is a fragmented perspective view of a dental tool for use in the formation of a channel and countersink in the understructure tooth portion;

FIG. 11 is a cross sectional view of a tooth or dentition with its surface excavated prior to building of a superstructure thereon, showing the channels with countersinks being formed in the understructure;

FIG. 12 is a sectional view similar to that shown in FIG. 11, illustrating the excavated tooth or dentition with one of two dental anchors being already inserted, and with the other dental anchor in the midst of being inserted; and FIG. 13 is a sectional view similar to that shown in FIGS. 11 and 12, illustrating the projection of the dental anchor of the present invention into the built up superstructure of the tooth or dentition.

In the various figures of the drawings, like reference characters designate like parts.

DETAILED DESCRIPTION OF THE PREFERRED EMBODIMENIS

Figure 1:
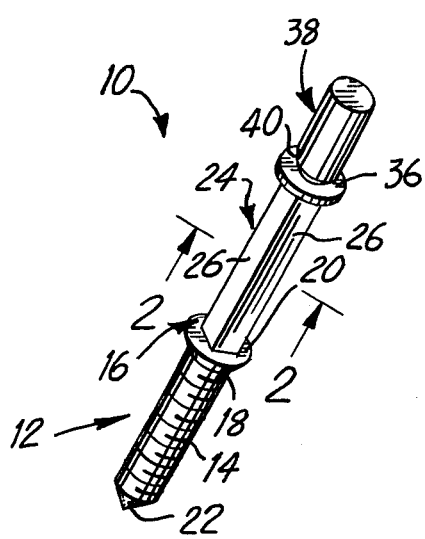
FIG. 1 is a perspective view illustrating one embodiment of the dental anchor in accordance with the present invention.

Referring now to the drawings, FIG. 1 shows a first embodiment comprising a dental anchor 10 in accordance with the present invention. The dental anchor 10 includes a lower anchoring portion 12 having a threaded section 14 and a depth-limiting section 16. Ihe anchoring portion 12 is screw-like, with the lower threaded section 14 being the threaded shank portion and the depth-limiting section 16 being the flat-head of the screw.

More particularly, the depth-limiting section 16 includes a frustro-conical shaped member having an outwardly flared periphery 18 terminating in the upper flat surface 20. At the lower end of the threaded section 14, there is provided a forward tip 22 to facilitate the insertion into a channel in a dentition understructure. The depth-limiting section 16 is such as to fit within a countersink formed in the tooth understructure.

Figure 2:
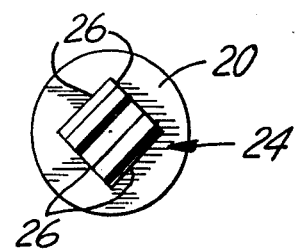
FIG. 2 is a sectional view taken along line 2—2 of FIG. 1, showing the cross sectional configuration of the retaining portion of the dental anchor.
Figure 3:
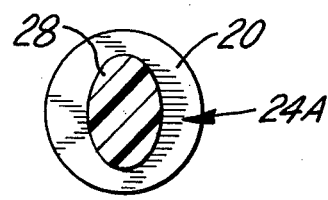
FIG. 3 is a sectional view similar to that shown in FIG. 2, showing an alternate cross sectional configuration.
Figure 4:
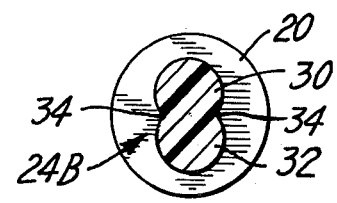
FIG. 4 is a sectional view similar to that shown in FIGS. 2 and 3, showing yet another alternate cross sectional configuration.

Integrally extending and coaxial with the anchoring portion 12, there is provided a retaining portion 24 which projects upwardly from the understructure and remains embedded in the superstructure tooth portion. It should be noted, that the retaining portion 24 has a cross-sectional configuration which is other than a round shape. As shown in FIGS. 1 and 2, it is noted that the shape of the retaining portion 24 is that of a square configuration having the four sides 26. However, for example, as shown in FIG. 3, the shape of the retaining portion 24A could also be that of an oval 28 and, as shown in FIG. 4, the shape of the retaining portion 24B could also be that of two circles 30, 32 which intersect along connecting or indentation lines 34 to define a cross sectional figure "8". Other non-circular configurations could also be utilized. The purpose of the non-circular configuration is to provide additional displacement-resistant means in order to prevent movement or displacement of the upper superstructure with respect of the tooth understructure.

At the upper end of the retaining portion 24, there is provided an annular collar 36 which is thin with respect to the thickness of the dental anchor, and which extends laterally outwardly with respect to dental anchor. The collar 36 provides additional retention means within the superstructure to prevent axial displacement of such superstructure with respect to the understructure.

At the upper end of the dental anchor is provided a manipulating end section 38 which is shown as a cylindrical section having a flat top end. However, numerous other types of manipulating end sections could be used, as is well known in the art; and as is described in my aforementioned patents. The manipulating end section 38 is interconnected to the retaining section 24, and particularly to the upper side of the collar 36 be means of a frangible, reduced thickness portion 40, so that the manipulating end section 38 can be severed from the rest of the dental anchor 10 after the lower anchoring portion 12 has been threaded into the channel of the tooth understructure.

Figure 5:
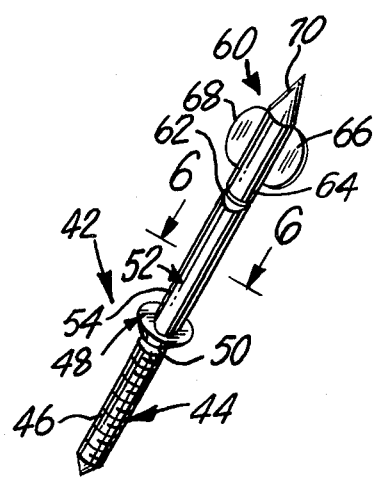
FIG. 5 is a perspective view illustrating an alternative embodiment of the dental anchor according to the present invention.

Referring now to FIG. 5, there is shown a second embodiment comprising a dental anchor 42 according to the present invention. The dental anchor 42 includes a lower anchoring portion 44 having a threaded section 46 with a depth-limiting section 48, as heretofore described. In this embodiment, wherein the dental anchor is machined, an undercut portion 50 is provided between the threaded section 46 and the depth-limiting section 48.

Figure 6:
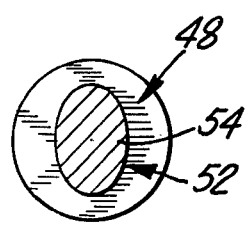
FIG. 6 is a cross sectional view taken along line 6—6 of FIG. 5, showing the cross sectional configuration of the retaining portion of the dental anchor of FIG. 5.
Figure 7:
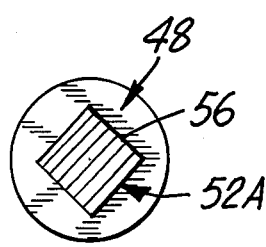
FIG. 7 is a sectional view similar to that shown in FIG. 6, showing another possible cross sectional configuration.
Figure 8:
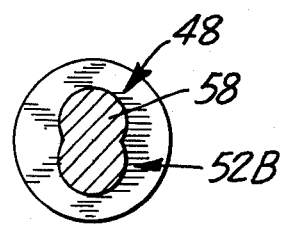
FIG. 8 is a sectional view similar to that shown in FIGS. 6 and 7, showing yet another possible cross sectional configuration.

Integral with, and axially extending from the anchoring portion 44 is a retaining portion 52 which will become embedded within the superstructure and is shaped to have other than a circular cross-sectional configuration in order to prevent displacement of the superstructure with respect to the understructure, as set forth above in connection with the retaining portion 24. For example, as shown in FIGS. 5 and 6, the particular shape of the retaining portion 52 is that of an oval 54. However, as shown in FIG. 7, a square configuration 56 could also be utilized for the retaining portion 52A. As shown in FIG. 8, a double circle or figure "8" configuration 58, could also be used for the retaining portion 52B, as heretofore described. Again, it should be appreciated, that other non-circular shapes could be utilized so as to provide the displacement resisting capability.

A manipulating end section 60 is coupled to the retaining section 52 by means of a frangible, reduced thickness portion 62. This reduced thickness portion 62 permits the manipulating section 60 to be severed from the remainder of the dental anchor 42 after the anchoring portion 44 has been inserted into the channel in the understructure. It is noted, that the reduced thickness portion 62 has a smaller diameter or dimension than the undercut portion 50 to insure the severance of the reduced thickness portion 62.

The particular manipulating end section 60 includes a cylindrical section 64 to which are connected a pair of wing portions 66, 68 laterally extending from the cylindrical section 64. These wing portions 66, 68 are shown as being connected tangentially to the cylindrical section 64. However, they could also extend axially therefrom. The wing portions 66, 68 provide torque transfer mechanisms which can be inserted into an appropriate manipulating tool or sleeve to permit insertion of the dental anchor into the tooth understructure. The upper end of the manipulating section is provided with a conical end 70 which functions as a pilot for inserting the manipulating end into a dental tool or sleeve. The particular manipulating end shown could also be varied so as to utilize the manipulating end section 38 of FIG. 1. Alternately, other types of manipulating ends, as described in my aforementioned patents, could also be utilized.

Although a manipulating end section has been shown coupled to the retaining portions, it should be appreciated, that since the retaining portion itself is non-circular, an appropriate dental tool could be coupled directly to the retaining portion whereby the retaining portion could simultaneously serve also as the manipulating portion. The tool would be coupled to the non-circular retaining portion, and the anchoring portion would then be inserted into the channel in the dental understructure. The tool would then be removed, and the retaining portion would then serve as that portion embedded in the tooth superstructure for displacement-resistant purposes.

It should also be appreciated that although the embodiment shown in FIG. 5 does not include the annular, laterally extending collar portion 36, shown in FIG. 1, such collar could also be included in the dental anchor of FIG. 5 to provide additional displacement and axial resisting benefits, as desired.

The particular material from which the dental anchor can be formed, can be any suitable materials usable in the dental art. However, as shown in FIGS. 1-4, such material can be plastic whereby the dental anchor can be molded. Typically, as shown in FIGS. 5-8, such material could be metal including precious metals or non-precious metals, such metals being well known in the art, whereby the dental anchor can be machined. The particular length of the various sections are such that the anchoring portion 12 is substantially equal to the retaining portion 24, including the collar 36. In FIG. 5, the anchoring portion 44 is substantially the same size as the retaining portion 52 up to the reduced thickness portion 62.

As will become clear hereinafter, the anchoring portion is threaded into a channel formed in the tooth understructure. The depth-limiting sections 16 or 48 will seat into a countersink formed at the upper end or mouth of the channel and thereby prevent the anchoring portion from bottoming-out in the channel. Such bottoming-out has been found to cause possible cracks in the tooth understructure. Accordingly, when the channel is formed in the tooth understructure, the countersink can be formed therewith.

Alternately, referring now to FIG. 9, the countersink can actually be formed by the dental anchor itself by modifying the depth-limiting sections 16, 48. As shown, the depth-limiting section 72 is formed at the upper end of the threaded lower anchoring section 74. The non-circular retaining portion 76 extends axially from the upper end of the depth-limiting section 72. Such depth-limiting section 72 is formed of a frustro-conical portion 78 which terminates at its upper end in a flat laterally extending annular surface 80. Positioned about the periphery of the frustro-conical portion 78 are a plurality of V-shaped notches 82, there being preferably four notches 82 extending inwardly from the outer surface. These notches 82 serve as teeth for self-cutting a countersink in the tooth understructure as the threaded anchoring portion 74 is being inserted into the channel.

The threading of the anchoring portion in the tooth understructure can be a self-threading type action for both the plastic and metal dental anchors, whereby only a longitudinal channel will initially be formed in the tooth understructure. Accordingly, the plastic dental anchor can be a compatible reinforced plastic capable of self-threading. Alternately, the channel itself can be prethreaded so that the dental anchor can be screwed into such a tapped hole.

In order to form the channel, it is important that the depth of the channel be greater than the axial length of the anchoring portion of the dental anchor in order to prevent bottoming-out of the anchor. Accordingly, the depth of the channel must be controlled. Referring now to FIG. 10, there is shown a dental tool which can facilitate formation of a channel for use in conjunction with the present dental anchors. Specifically, there is shown a dental tool 84 which includes a conventional shank portion 86 from which extends a blade 88. The blade 88 is formed of a thin piece of metal 90 which has been twisted 360 degrees. As a result, the upper surface 92 extending outwardly from the shank portion 86, goes through a first twist of 180 degrees whereby it appears on the underside in the medial portion of the blade 88, and again reappears as the upper surface 92 in the distal end of the blade 88. The forward end of the blade has its lateral edges 94, 96 tapered to provide a pointed tip 98. The blade 88 itself serves as a twist drill for forming a channel extending into the tooth understructure. At the inner end of the blade, which extends from the shank portion 86, the lateral edges 100, 102 are outwardly flared, so that as the twist drill forms the channel, a countersink will simultaneously be formed at the mouth of the channel. The depth of the channel is controlled by the length of the blade 88. The forward end face 104 of the shank portion 86 serves as a natural stop for the twisting action of the blade 88 to thereby limit the channel depth to a desired amount.

Typically, the blade 88 is embedded into the shank portion 86 which can be plastic, metal or other material, as is known in the art. The dental tool 84 can be hand held by means of an additional handle, of the type described in my aforementioned patents, or can be formed such as to fit into a conventional dental hand-piece of a rotating drill.

Referring now to FIGS. 11-13, the use of the present apparatus in connection with providing a superstructure to a tooth will be described. In the figures, there is shown a tooth or dentition 106 in the soft tissue or gingiva 108 of the human gum. As is well known to those skilled in the art, the body of the tooth is formed of dentin 110 and encloses a pulp channel 112. The dentin 110 projecting from the gingiva is covered by a layer 114 of enamel. In order to prepare the dentition for building a superstructure thereon, a portion of the enamel 114 and a portion of the dentin 110 are excavated to thereby remove decayed and undermined understructure and form an excavated surface 116 free of decay.

In order to provide a superstructure, a plurality of channels 118 are formed extending into the dentin 110 from the excavated surface 116. For this purpose, the twist drill 84, heretofore shown in FIG. 10, is twisted into the dentin 110 as shown in FIG. 11. In the formation of the channel 118, by means of the twist drill 84, a countersink 120 will simultaneously be formed at the surface 116.

The number of channels needed in a particular understructure will vary with the area of the excavated surface 116, and the portion of a superstructure that must be placed. Typically, as is known in the prior art, the channels 118 will be angularly formed in the understructure so that the dental anchors which are inserted therein, will be angularly positioned to provide additional displacement resistant properties.

After the appropriate number of channels 118 have been formed, either of the dental anchors 10, 42 pursuant to the present invention are inserted into the channels 118, the dental anchors 10 being shown by way of example. If the anchoring portions are self-threading, they will automatically thread into the channels 118. On the other hand, if the anchoring portions are not self-threading, a tapped hole will first be provided in the channels 118 to receive the threaded dental anchors.

The dental anchors 10 are inserted by utilizing the manipulating sections 38 extending at the distal ends of the dental anchor. The particular tool utilized for insertion can be any of the convetional known tools for such purpose, and the particular tool will depend upon the type of manipulating end portion provided on the dental anchor. The dental anchor is inserted until the depth-limiting portion 16 seats into the countersink 120 at the mouth of the channel.

As can be noted in FIG. 12, the dental anchor 10 on the left of the tooth structure has already been inserted in place on the dental understructure. The dental anchor 10 on the right, on the other hand, is in the process of being inserted. It should be noted, that the left hand dental anchor, which is already inserted, does not bottom-out at the bottom of the channel 118. Specifically, the bottom 122 of the channel 118 extends to a lower depth which is spaced from the lower tip 22 of the threaded portion 14 of the dental anchor 10. Thus, bottoming-out is prevented by the depth-limiting portion 16 which seats into the countersink 120 and prevents further insertion of the anchoring portion into the channel 118. By preventing bottoming-out of the anchor, cracks in the lower portion of the tooth can be avoided.

In the example shown, the countersink was formed by means of the drill 84 simultaneous with the formation of the channel 118. It should be appreciated, that if the dental anchor having the depth-limiting section 72 of the type shown in FIG. 9 was utilized, the countersinks 120 would not have to be formed in the understructure, whereby the threading of the dental anchor in the tooth understructure would cause the depth-limiting section 72 to simultaneously form the countersink 120. The depth-limiting section 72 would then sit in the countersink 120 that it forms itself, and again prevent further insertion of the dental anchor into the channel 118 so as to again avoid bottoming out of the dental anchor.

After the dental anchor 10 has been suitably inserted into the tooth understructure, the manipulating portion 38 is severed from the remaining dental anchor along the frangible reduced diameter portion 40. After the manipulating portion 38 has been severed, it should be noted that the retaining portion 24 of the anchor, together with the collar 36, if one is proveded, will project above the tooth understructure so as to be available for embedding within the superstructure which will be built up thereon, as shown in FIG. 13.

Ihe final step in the process is now to build a superstructure onto the exposed excavated surface now provided with the projections extending above the tooth understructure. As shown in FIG. 13, such superstructure 124 is so formed relative to the understructure 106 so as to effectively restore the tooth structure. It should be appreciated, that the upper retaining portions 24 of the anchors, as well as the collar 36, are embedded in such superstructure and provide a displacement resistant attachment of the superstructure to the understructure. As is known in the art, the retaining portions 24 projecting from the understructure could also be bent to provide further angular orientation of the dental anchors in order to further enhance the displacement resistant properties.

Numerous alterations of the structure herein disclosed will suggest themselves to those skilled in the art. However, it is to be understood that the present disclosure relates to preferred embodiments of the invention which are for purposes of illustration only and are not to be construed as a limitation of the invention.

What is claimed is:

1. A dental anchor for securing a superstructure to a tooth understructure, comprising:

an elongated anchoring portion having a specific length for insertion within a channel extending into the tooth understructure, the channel having a predetermined length greater than said specific length of said anchoring portion;

said anchoring portion including a threaded section;

a coaxial, elongated retaining portion having a non-circular cross section for embedding within the superstructure;

depth-limiting means integrally disposed between said anchoring portion and said retaining portion for limiting depth of insertion of said anchoring portion into the channel so that said anchoring portion is spaced from a bottom of the channel;

a manipulating end portion for facilitating insertion of said anchoring portion into the channel;

a frangible reduced thickness portion interposed between said manipulating end portion and said retaining portion to permit severing of said manipulating end portion from said retaining portion after said anchoring portion is inserted into said channel; and said depth-limiting means including a frustro-conical section outwardly flaring from said elongated anchoring portion for seating in a countersink at an upper end of the channel in the understructure;

whereby the seating of said frustro-conical section in the channel countersink causes the severing of said manipulating end portion from said retaining portion.

2. A dental anchor as in claim 1, and further comprising an integral collar interposed between said retaining portion and said reduced thickness portion, and extending laterally of said elongated retaining portion.

3. A dental anchor as in claim 2, wherein said collar is circular.

4. A dental anchor as in claim 1, wherein the periphery of said frustro-conical section includes a plurality of elongated notches for self-forming the countersink in the understructure.

5. A dental anchor as in claim 1, and further comprising an undercut interposed between said frustro-conical section and said anchoring portion.

6. A dental anchor as in claim 1, wherein the elongate extent of said retaining portion substantially equals the combined elongate extent of said anchoring portion and said depth-limiting means.

7. A dental anchor as in claim 1, wherein said retaining portion has a substantially square cross-sectional configuration.

8. A dental anchor as in claim 1, wherein said retaining portion has a substantially oval cross-sectional configuration.

9. A dental anchor as in claim 1, wherein said retaining portion has a cross-sectional configuration of two intersecting circles to define a figure "8".

10. A dental anchor as in claim 1, wherein said threaded section of said anchoring portion is self-threading.

11. A dental anchor as in claim 1, wherein said manipulating end portion includes an elongate section having a substantially circular cross-sectional configuration.

12. A dental anchor as in claim 11, wherein said manipulating end portion further includes a pair of wing portions laterally extending in opposite directions from said elongate section.

13. A dental anchor as in claim 1, wherein said dental anchor is fabricated from a plastic material.

* * * * *